United States Patent [19]
Xu et al.

[11] Patent Number: 5,721,126
[45] Date of Patent: Feb. 24, 1998

[54] METHOD FOR CLONING AND PRODUCING THE SCAI RESTRICTION ENDONUCLEASE IN *E. COLI*

[75] Inventors: Shuang-Yong Xu, Lexington; Jian-Ping Xiao, Wenham, both of Mass.

[73] Assignee: New England Biolabs, Inc., Beverly, Mass.

[21] Appl. No.: 569,806

[22] Filed: Dec. 8, 1995

[51] Int. Cl.$^6$ .......................... C12N 9/22; C12N 15/55; C12N 15/70

[52] U.S. Cl. ............... 435/199; 435/252.3; 435/252.33; 435/320.1; 536/23.2

[58] Field of Search .................. 435/320.1, 252.3, 435/252.33, 199; 536/23.2

[56] References Cited

FOREIGN PATENT DOCUMENTS 0 193 413  12/1993  European Pat. Off. .

OTHER PUBLICATIONS

Kosykh, et al., Molec. Gen. Genet., 178;717–719 (1980).
Mann, et al., Gene, 3:97–112 (1978).
Walder, et al., Proc. Nat. Acad. Sci., 78;1503–1507 (1981).
Bougueleret, et al., Nucl. Acids. Res., 12:3659–3676 (:1984).
Gingeras and Brooks, Proc. Nat. Acad. Sci., 80:402–406 (1983).
Theriault and Roy, Gene, 19:355–359 (1982).
Blumenthal, et al., J. Bacteriol., 164:501–509 (1985).
Kiss, et al., Nucl. Acids Res., 13:6403–6421 (1985).
Szomolanyi, et al., Gene, 10:219–225 (1980).
Janulaitis, et al., Gene, 20:197–204 (1982).
Kiss and Baldauf, Gene, 21:111–119 (1983).
Walder, et al., J. Biol. Chem., 258:1235–1241 (1983).
Fomenkov, et al., Nucl. Acids Res., 22:2399–2403 (1994).
Raleigh and Wilson, Proc. Natl. Acad. Sci., 83:9070–9074 (1986).
Skoglund, et al., Gene, 88:1–5 (1990).

*Primary Examiner*—Charles L. Patterson, Jr.
*Attorney, Agent, or Firm*—Gregory D. Williams

[57] ABSTRACT

The present invention relates to isolated DNA coding for the restriction endonuclease SCaI as well as to a method for cloning methylase genes from Streptomyces into *E. coli* by a modification of the methylase selection method. At first, the standard methylase gene selection method was tried to clone the SCaI methylase gene using a high-copy-number cloning vector pUC19 during library construction. The SCaI methylase gene was refractory to cloning by using pUC19, presumably due to the poor expression of the SCaI methylase gene in *E. coli*. If the SCaI methylase is not efficiently expressed in *E. coli*, the SCaI sites on the plasmid will not be sufficiently modified by the methylase. As a consequence, the plasmid will be cleaved and lost in the plasmid library after SCaI endonuclease challenge. Since the standard methylase selection did not work, the "endo-blue method" was tried to clone the SCaI endonuclease gene. Nineteen blue colonies were identified, but none of them yielded any detectable SCaI endonuclease activity. The SCaI endonuclease gene was first cloned by inverse PCR using primers that annealed to the end of the SCaI methylase gene. In order to increase the SCaI endonuclease expression in *E. coli*, an optimal ribosome binding site and spacing were engineered in front of the ATG start codon and the gene was inserted into expression vector pRRS.

7 Claims, 4 Drawing Sheets

```
ATGTCCGGGCGGGACTTTGGATATGTGATACAGTCGTCCGCTGCACTATGGAATCGACTC
 M  S  G  R  D  F  G  Y  V  I  Q  S  S  A  A  L  W  N  R  L
TCTACATTCTCACAGAGAGGAAAAGCCTTGGACACCAGGCTTGCAGACATCAAGAAGGCC
 S  T  F  S  Q  R  G  K  A  L  D  T  R  L  A  D  I  K  K  A
CTGGGGAAGCCGTACTACGAAACCTCGGATGTCCTTCTTTACCACGGCGACAGTCTTGAG
 L  G  K  P  Y  Y  E  T  S  D  V  L  L  Y  H  G  D  S  L  E
CTGCTCAAGTCAATGCCTCAGCAGATTTTCGACCTTACCGTAACTAGTCCACCTTACAAT
 L  L  K  S  M  P  Q  Q  I  F  D  L  T  V  T  S  P  P  Y  N
ATTGGCAAAGAGTACGAGGGTGTACTGTCGATCGAGGAATACATTTCCTGGTGCGAGACA
 I  G  K  E  Y  E  G  V  L  S  I  E  E  Y  I  S  W  C  E  T
TGGATGTCGCGCGTTCATAGGGCGACCAGCGCAGGCGGCGCATTTTGGCTCAATGTTGGG
 W  M  S  R  V  H  R  A  T  S  A  G  G  A  F  W  L  N  V  G
TACGTCCCTGTCCCGAACCAAGGAAAAGCAGTCCCGATTCCTTACCTCTTGTGGGACAAG
 Y  V  P  V  P  N  Q  G  K  A  V  P  I  P  Y  L  L  W  D  K
AGTCCGTTCTACATGATCCAGGAAGTTGTCTGGAATTACGGGGCGGGAGTGGCGTCTCGA
 S  P  F  Y  M  I  Q  E  V  V  W  N  Y  G  A  G  V  A  S  R
AAATCGTTTTCCCCGCGCAATGAAAAGTTTCTCTGGTATGTGCGCGACCCGCTGAATTAT
 K  S  F  S  P  R  N  E  K  F  L  W  Y  V  R  D  P  L  N  Y
TACTTCGACCTCGATTCGGTGCGCGACCCAAATGTGAAATACCCCAACCAGAAAAAGAAT
 Y  F  D  L  D  S  V  R  D  P  N  V  K  Y  P  N  Q  K  K  N
GGGAAGCTCAAATGCAACCCGTTGGGGAAAAATCCCACTGACGTTTGGCAGTTCCCCAAG
 G  K  L  K  C  N  P  L  G  K  N  P  T  D  V  W  Q  F  P  K
GTTACGTCGGGCGCGAAGAGATCAAGCGTGGAGCGCACCGCCCATCCGGCACAATTCCCG
 V  T  S  G  A  K  R  S  S  V  E  R  T  A  H  P  A  Q  F  P
TCTGCAGTCATTGAACGGGTCATCAAGGCGTGCAGCCCTTCCGACGGCGTCATCCTGGAC
 S  A  V  I  E  R  V  I  K  A  C  S  P  S  D  G  V  I  L  D
CCATTCCTCGGTTCCGGAACGACCTCGCTGACCGCCAGAAAGCAAGGCCGGTGCAGCGTC
 P  F  L  G  S  G  T  T  S  L  T  A  R  K  Q  G  R  C  S  V
GGTATCGAAATCCGCGAAGACTACCTCGACATCGCGGTGGGACGCCTGGAGGCGGAGGCG
 G  I  E  I  R  E  D  Y  L  D  I  A  V  G  R  L  E  A  E  A
CAATCCCTCTTCTAG
 Q  S  L  F  *
```

FIG. 2

```
ATGATCAACGATCAGCTTCCCCGGTGGGTGCGCGAGGCGCGCGTGGGTACAAGAACAGGC
 M  I  N  D  Q  L  P  R  W  V  R  E  A  R  V  G  T  R  T  G
GGCCCTGCAATGCGCCCGAAAACTTCCGATTCGCCCTACTTTGGATGGGATAGCGAAGAT
 G  P  A  M  R  P  K  T  S  D  S  P  Y  F  G  W  D  S  E  D
TGGCCCGAAGTGACTCGCCAGCTACTGTCCGAGCAACCGCTCAGCGGCGACACGCTTGTC
 W  P  E  V  T  R  Q  L  L  S  E  Q  P  L  S  G  D  T  L  V
GATGCCGTGCTCGCTTCGTGGGAATCGATCTTCGAATCCCGGCTGGGGAGCGGATTTCAC
 D  A  V  L  A  S  W  E  S  I  F  E  S  R  L  G  S  G  F  H
ATCGGCACCCAGATCCGGCCGACTCCACAAGTAATGGGATTCCTCCTTCATGCACTCATC
 I  G  T  Q  I  R  P  T  P  Q  V  M  G  F  L  L  H  A  L  I
CCTCTTGAGCTCGCCAACGGCGACCCGAGCTGGCGCGCGGACCTGAATTCCTCCGAAAAG
 P  L  E  L  A  N  G  D  P  S  W  R  A  D  L  N  S  S  E  K
GATCTCGTGTATCAGCCGGATCATAAATATTCAATCGAGATGAAAACCTCGTCACACAAG
 D  L  V  Y  Q  P  D  H  K  Y  S  I  E  M  K  T  S  S  H  K
GATCAAATTTTCGGCAACCGAAGCTTCGGAGTCGAGAATCCCGGCAAGGGAAAGAAGGCA
 D  Q  I  F  G  N  R  S  F  G  V  E  N  P  G  K  G  K  K  A
AAGGACGGCTATTATGTGGCGGTAAACTTCGAAAAATGGAGTGACGCTCCGGGCAGACTT
 K  D  G  Y  Y  V  A  V  N  F  E  K  W  S  D  A  P  G  R  L
CCACGCATCCGGACGATCCGCTATGGGTGGCTTGACCATACAGATTGGGTGGCGCAGAAA
 P  R  I  R  T  I  R  Y  G  W  L  D  H  T  D  W  V  A  Q  K
TCTCAAACGGGCCAGCAGTCGTCACTACCGGCCGTCGTATCCAACACTCAACTCCTCGCC
 S  Q  T  G  Q  Q  S  S  L  P  A  V  V  S  N  T  Q  L  L  A
ATCCATACGGGTGGCCAGAGGTAA
 I  H  T  G  G  Q  R  *
```

FIG. 3

METHOD FOR CLONING AND PRODUCING THE SCAI RESTRICTION ENDONUCLEASE IN E. COLI

BACKGROUND OF THE INVENTION

The present invention relates to recombinant DNA which encodes the SCaI restriction endonuclease and modification methylase, and the production of SCaI restriction endonuclease from the recombinant DNA.

Type II restriction endonucleases are a class of enzymes that occur naturally in bacteria. When they are purified away from other bacterial components, restriction endonucleases can be used in the laboratory to cleave DNA molecules into precise fragments for molecular cloning and gene characterization.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. Over one hundred and eighty restriction endonucleases with unique specificities have been identified among the many hundreds of bacterial species that have been examined to date.

Bacteria tend to possess at most, only a small number of restriction endonucleases per species. The endonucleases typically are named according to the bacteria from which they are derived. Thus, the species *Deinococcus radiophilus* for example, synthesizes three different restriction endonucleases, named DraI, DraII and DraIII. These enzymes recognize and cleave the sequences TTTAAA (SEQ ID NO:1), PuGGNCCPy (SEQ ID NO:2) and CACNNNGTG (SEQ ID NO:3), respectively. *Escherichia coli* RY13, on the other hand, synthesizes only one enzyme, EcoRI, which recognizes the sequence GAATTC (SEQ ID NO:4).

It is thought that in nature, restriction endonucleases play a protective role in the welfare of the bacterial cell. They enable bacteria to resist infection by foreign DNA molecules like viruses and plasmids that would otherwise destroy or parasitize them. They impart resistance by cleaving invading foreign DNA molecule each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one or other of the nucleotides within the sequence by the addition of a methyl group. Following methylation, the recognition sequence is no longer cleaved by the restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction o endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet* 178: 717–719, (1980); HhaII: Mann et al., *Gene* 3: 97–112, (1978); PstI: Walder et al., *Proc. Nat. Acad. Sci.* 78 1503–1507, (1981), the disclosures of which are hereby incorporated by reference herein). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12: 3659–3676, (1984); PaeR7: Gingeras and Brooks, *Proc. Natl. Acad. Sci. USA* 80: 402–406, (1983); Theriault and Roy, *Gene* 19: 355–359 (1982); PvuII: Blumenthal et al., *J. Bacteriol* 164:501–509, (1985), the disclosures of which are hereby incorporated by reference herein).

A third approach, and one that is being used to clone a growing number of systems are now being cloned by selection for an active methylase gene (refer to our EPO No.: 193,413 published, Sep. 3, 1986 and BsuRI: Kiss et al., *Nucl. Acid. Res.* 13:6403–6421, (1985), the disclosures of which are hereby incorporated by reference herein). Since restriction and modification genes are often closely linked, both genes can often be cloned simultaneously. This selection does not always yield a complete restriction system however, but instead yields only the methylase gene (BspRI: Szomolanyi et al., *Gene* 10: 219–225, (1980); Bcn I: Janulaitis et al, *Gene* 20:197–204 (1982); Bsu RI: Kiss and Baldauf, *Gene* 21: 111–119, (1983); and Msp I: Walder et al., *J. Biol. Chem.* 258: 1235–1241, (1983), the disclosures of which are hereby incorporated by reference herein).

A more recent method (the "endo-blue method") has been described for direct cloning of restriction endonuclease genes in *E. coli* based on the indicator strain of *E. coli* containing the dinD::lacZ fusion (Fomenkov et al., *Nucl. Acids Res.* 22: 2399–2403 (1994), the disclosure of which is hereby incorporated by reference herein). This method utilizes the *E. coli* SOS response following DNA damages by endonucleases or non-specific nucleases. A number of thermostable nuclease genes (TaqI, TthI111 I, BsoBI, Tf nuclease) have been cloned by this method.

Another obstacle to cloning these systems in *E. coli* was discovered in the process of cloning diverse methylases. Many *E. coli* strains (including those normally used in cloning) have systems that resist the introduction of DNA containing cytosine methylation. (Raleigh and Wilson, *Proc. Natl. Acad. Sci., USA* 83: 9070–9074, (1986), the disclosure of which is hereby incorporated by reference herein). Therefore, it is also necessary to carefully consider which *E. coli* strain(s) to use for cloning.

When foreign restriction modification systems are cloned and introduced into *E. coli*, sometimes the methylase and endonuclease expressions are quite low compared to the native endonuclease-producing strains, probably due to poor transcription or translation of the genes in *E. coli*. This is particularly true for cloning of Streptomyces genes into *E. coli* because of the different GC contents of the two microorganisms. It would be desirable to have a cloning system that Streptemyces genes can be sufficiently expressed in *E. coli* and selected for based on the efficient gene expression.

Because purified restriction endonucleases, and to a lesser extent, modification methylases, are useful tools for characterizing genes in the laboratory, there is a commercial incentive to obtain bacterial strains through recombinant DNA techniques that synthesize these enzymes in abundance. Such strains would be useful because they would simplify the task of purification as well as providing the means for production in commercially useful amounts.

SUMMARY

The present invention relates to isolated DNA coding for the restriction endonuclease SCaI as well as to a method for cloning methylase genes from Streptomyces into *E coli* by a modification of the methylase selection method. At first, the standard methylase gene selection method was tried to clone the SCaI methylase gene using a high-copy-number cloning vector pUC19 during library construction. The SCaI methylase gene was refractory to cloning by using pUC19, presumably due to the poor expression of the SCaI methylase gene in *E. coli*. If the SCaI methylase is not efficiently expressed in *E coli*, the SCaI sites on the plasmid will not be sufficiently modified by the methylase. As a consequence, the plasmid will be cleaved and lost in the plasmid library after SCaI endonuclease challenge. Since the standard methylase selection did not work, the "endo-blue method" was tried to clone the SCaI endonuclease gene. Nineteen blue colonies were identified, but none of them yielded any detectable SCaI endonuclease activity.

In order to increase SCaI methylase gene expression in *E. coli*, a high-copy-number plasmid containing a lacUV5 promotor called pRRS (Skoglund et al. *Gene* 88: 1–5 (1990), the disclosure of which is hereby incorporated by reference herein) was used to clone the SCaI methylase gene and the resulting library DNA was used for methylase selection. The SCaI methylase gene was successfully cloned in pRRS in four steps: (1) ligation of Sau3AI partially digested genomic DNA and BamHI-cleaved and CIP treated pRRS and transformation of the ligated DNA into *E. coli* RR1 competent cells; (2) preparation of mixed plasmid library; (3) SCaI digestion of plasmid DNA library and retransformation of the challenged DNA into RR1 cells; (4) Screening SCaI resistant plasmid(s) among the survivors. After the SCaI methylase gene was cloned, efforts were made to clone DNA fragments on both sides of the methylase gene. Usually methylase gene and endonuclease gene in a particular restriction-modification system are located next to each other. DNA at the left side of the SCaI methylase gene was cloned by DNA amplification with inverse PCR. The DNA was sequenced and translated in all six reading frames. The translated protein sequences were compared with the N-terminus protein sequence of the partially purified SCaI protein. One predicted protein sequence matches closely with the N-terminal sequence of the SCaI protein. The entire SCaI endonuclease gene was cloned by amplifying the gene with polymerase chain reaction from genomic DNA, ligated into pRRS vector and transformed into SCaI methylase premodified *E. coli* strain.

BRIEF DESCRIPTION OF THE FIGURES

FIG. 2 is the DNA sequence (SEQ ID NO:5) of scaIM gene and its encoded protein sequence (SEQ ID NO:6).

FIG. 3 is the DNA sequence (SEQ ID NO:7) of scaIR gene and its encoded protein sequence (SEQ ID NO:8).

DETAILED DESCRIPTION OF THE INVENTION

Figure 1:
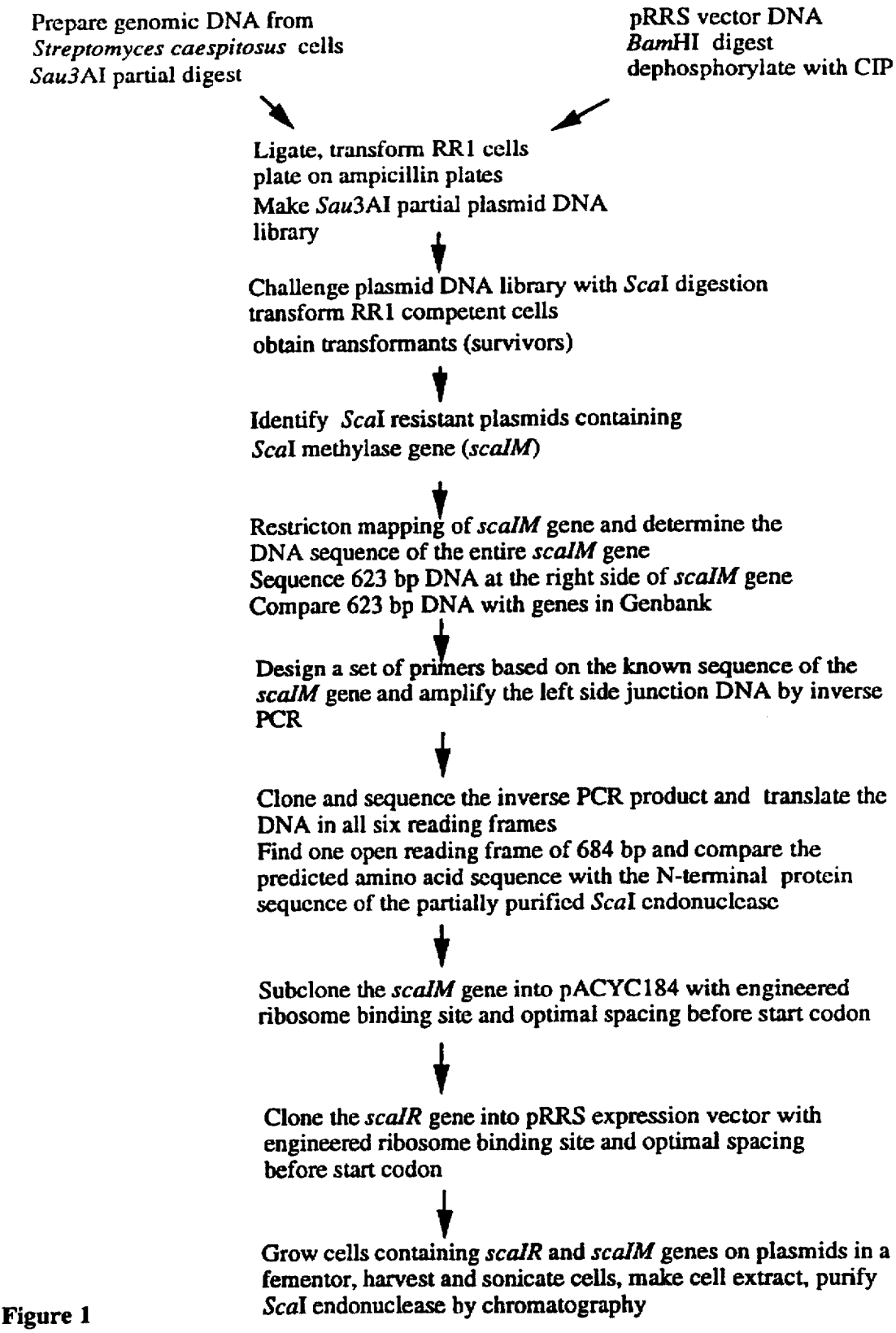
FIG. 1 is a scheme for cloning and producing the SCaI restriction endonuclease.
Figure 4:
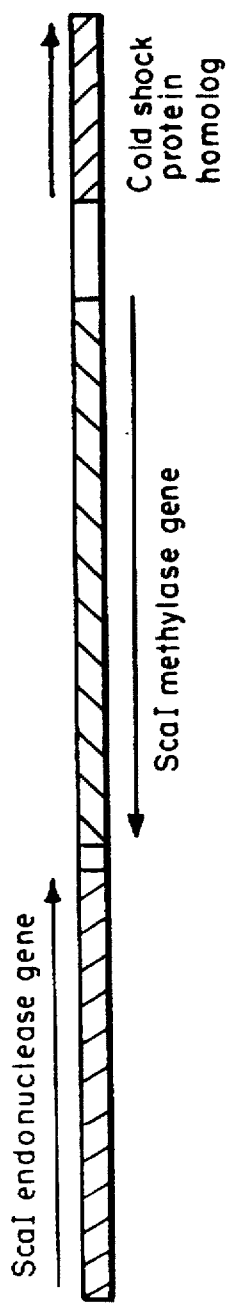
FIG. 4 is the organization of the SCaI restriction-modification system.

The method described herein by which the SCaI methylase gene and endonuclease gene are cloned and expressed is illustrated in FIG. 1 and includes the following steps:

1. The genomic DNA of *Streptomyces caespitosus* is purified.

2. The DNA is digested partially with a restriction endonuclease such as Sau3AI, or any of its isoschizomers, that generates a DNA fragment(s) containing the entire SCaI methylase gene. The fragment(s) should also be of clonable size, that is, between 1–20 kb.

3. The Sau3AI-digested genomic DNA is preferably ligated into BamHI-cleaved/CIP treated high expression vectors such as pRRS. Other vectors with $P_{tac}$, $\lambda P_L$, $\lambda P_R$ promoters can also be used. The resulting mixtures are used to transform an appropriate host, i.e. a hsdR[31], mcrBC[31], mrr⁻ strain, such as *E. coli* strain RR1. The DNA/cell mixtures are plated on ampicillin selective media for transformed cells. After incubation, the transformed cells are pooled together to form the primary cell library.

4. The recombinant plasmids are purified in toto from the primary cell library to make primary plasmid library. The purified plasmid library is then digested to completion in vitro with SCaI endonuclease, or any SCaI isoschizomer. SCaI endonuclease digestion causes the selective destruction of unmodified, non-methylase-containing clones, resulting in an increase in the relative frequency of SCaI methylase-carrying clones.

5. Identification of SCaI methylase clone: The digested plasmid library DNA is transformed back into a host such as *E coli* strain RR1 and transformed colonies are again obtained by plating on ampicillin plates. The colonies are picked and their plasmid DNA is prepared and analyzed for the presence of the SCaI methylase gene by incubating purified plasmid DNA in vitro with SCaI endonuclease to determine whether it is resistant to SCaI digestion.

6. Once it has been established that the methylase gene has been cloned, the clone is analyzed by restriction mapping and deletion mapping. The region containing the scaIM gene is sequenced.

7. A total of 623 bp DNA was sequenced at the right side of the SCaI methylase gene. This DNA sequence was compared with all known genes in Genbank database using program "Blastx". The sequence comparison showed that one predicted open reading frame (unfinished) from this 623 bp has some homology to *E. coli* cold shock protein. It was concluded that the DNA at the right side of the SCaI methylase gene could not be the SCaI endonuclease gene.

8. To clone the left side junction DNA, *Streptomyces caespitosus* genomic DNA is digested with BsaWI, BspEI, NlaIII, PstI, PvuI, Sau3AI, and SpeI restriction enzymes or any other restriction enzymes that will give rise to reasonable size template DNA (less than 3 kb) for inverse PCR reaction. The digested DNA are self-ligated at a low DNA concentration (less than 2 µg per ml). The ligated circular DNA is used as templates for inverse PCR reaction using a set of primers that annealed to the end of the SCaI methylase gene. Following the above protocol, a 1.6 kb inverse PCR product is obtained from PvuI cleaved and self-ligated genomic DNA. The DNA is treated with T4 polynucleotide kinase and T4 DNA polymerase and cloned into HincII-cleaved/CIP treated pUC19 vector. The entire insert is sequenced the DNA sequences are translated into amino acid sequences in all six reading frames and then compared with the SCaI N-terminus protein sequence. This approach produces one open reading frame of 684 bp that has six amino acids identity with the actual SCaI protein sequence.

9. The SCaI methylase gene is then cloned into a compatible plasmid pACYC184 to premodify E. coli host. In order to increase the translation efficiency in E. coli, an efficient ribosome binding site and optimal spacing are engineered in front of the methylase gene. The entire SCaI endonuclease gene is amplified by PCR with two primers. The forward primer contains the ribosome binding site and 6 bp spacing before the ATG start codon. The SCaI endonuclease gene is cloned into expression vector pRRS and transformed into SCaI methylase premodified cells.

10. E. coli cells containing pACYC184-SCaIM$^+$ and pRRS-SCaIR$^+$ are grown to stationary phase at 30° C. overnight. Cells are harvested and lysed by sonication. Cell extracts are assayed for SCaI endonuclease activity. SCaI endonuclease is purified by chromatography.

The following Example is given to illustrate embodiments of the present invention as it is presently preferred to practice. It will be understood that this example is illustrative, and that the invention is not to be considered as restricted thereto except as indicated in the appended claims.

EXAMPLE 1

CLONING OF SCaI RESTRICTION-MODIFICATION SYSTEM

1. SCaI methylase selection using pUC19 as a cloning vector.

One SCaI linker was inserted into the SspI site of pUC19 The modified pUC19 was used for library construction. Sau3AI partially digested S. caespitosusgenomic DNA were ligated to BamHI cleaved/CIP treated pUC19 DNA. SmaI partially digested and completely digested genomic DNA was ligated with SmaI cut/CIP treated pUC19 DNA. Ligated DNA mixtures were transformed into RR1 competent cells and plated on Ampicillin plates. A total of 13,600 and 60,000 cells were found in SmaI and Sau3AI libraries, respectively. Plasmid DNA was prepared from each primary cell library. 5 µg, 2 µg, and 1 µg of the library DNA was cleaved with 100 units of SCaI restriction endonuclease at 37° C. for two hours. The SCaI-challenged DNA was retransformed into RR1 competent cells. Plasmid DNA was isolated again from the surviving transformants and digested with SCaI restriction enzyme to see if the plasmid DNA is resistant to SCaI digestion. 144 plasmid isolates from the Sau3AI library and 58 plasmid isolates from the SmaI library were analyzed for resistance to SCaI digestion. Five resistant clones were found that have lost one or both SCaI sites in the vector. No true resistant clones (methylase carrying clones) were found in these two libraries.

2. Attempt to clone SCaI endonuclease gene using the "endo-blue method".

It was reasoned that if the SCaI endonuclease gene is poorly expressed in E. coli cell, one could use the "endo-blue method" to clone the endonuclease gene directly into E. coli without the SCaI methylase protection. Sau3AI partially digested SCaI genomic DNA was ligated to BamHI-digested/CIP treated pUC19 and transformed into E. coli indicator strain carrying din 1::lacZ fusion and plated on X-gal indicator plates. Nineteen blue colonies were found among 5,000 Ap$^R$ transformants. The individual blue colony was inoculated into 10 ml LB plus Ap and shaken overnight at 30° C. Cell were harvested and resuspended in 1 ml of sonication buffer plus lysozyme (100 µg/ml). 1 µl, 2.5 µl, 5 µl, and 10 µl of the cell extract were used to cut 1 µg of λ DNA at 37° C. for one hour. No SCaI activity was found in the cell extracts of all the blue isolates. It was concluded that none of the clones contained the SCaI endonuclease gene or the endonuclease gene was not expressed well for in vitro detection.

3. SCaI methylase selection using pRRS as a cloning vector.

The methylase selection method requires that the SCaI methylase gene to be expressed to a reasonal level in vivo so that the methylase can modify the SCaI site on the vector that carries the SCaI methylase gene. It is known that Streptomyces genes are poorly expressed in E. coli due to the different GC contents of the two microorganisms. In order to express the SCaI methylase gene to a high level, another high-copy-number vector pRRS was used as a cloning vehicle. Plasmid pRRS carries the lacUV5 promotor which is stronger than the regular lac promotor in pUC19. Genes cloned into the multiple cloning sites are driven by the lacUV5 promotor. Sau3AI partially digested S. caespitosus genomic DNA was ligated to the BamHI digested/CIP treated pRRS vector and the ligated DNA transformed into RR1 competent cells. A total of 18,000 of Ap$^R$ transformants were obtained as the primary cell library. Plasmid DNA was prepared from the primary cell library. Five µg of the library DNA was cleaved with 100 units of SCaI restriction enzyme, and transformed back into RR1 competent cells. The surviving transformants were picked and cultured. Plasmid DNA was isolated from cultures of the individual cells. To examine if any one of these plasmids contain SCaI methylase gene, 78 individual plasmids were digested with SCaI endonuclease. #37, #38, and #54 plasmids were found to be truely resistant to SCaI digestion. #54 plasmid carries approximately 5000 bp insert and it was analyzed further. A 1.7 kb SacI fragment deletion clone still contains the active methylase gene. Deletion of a PstI fragment (about 2 kb) of the insert inactivate the SCaI methylase gene and render the deletion clones sensitive to SCaI endonuclease cleavage. It was concluded that one PstI site is located within the SCaI methylase gene. Efforts were made to sequence the DNA surrounding the PstI site. Three subclones (SacI to PstI, HindIII to PstI, and PstI to PstI) were constructed using pUC19 vector. The DNA sequence was determined using universal forward and reverse primers of pUC19. The remaining DNA was sequenced by primer walking. One open reading frame was identified that contains methylase motifs SPPY(SEQ ID NO:9) and DPFLGSGTT (SEQ ID NO:10). The methylase gene was coded by the bottom strand and runs in the reverse orientation.

In order to identify the SCaI endonuclease gene, 623 bp of DNA at the right side of the methylase gene was sequenced. This stretch of DNA was compared with all known genes in Genbank. It was found that one partial open reading frame within the 623 bp has some homology with a gene coding for a cold shock protein of *E. coli*. Therefore, efforts were concentrated on cloning and sequencing DNA at the left side of the methylase gene.

4. Cloning of SCaI endonuclease gene

Cloning of SCaI endonuclease gene by inverse PCR: Inverse PCR is an efficient way to clone adjacent DNA to the known DNA sequence. *S. caespitosus* genomic DNA was digested with BsaWI, BspEI, NlaIII, PstI, PvuI, Sau3AI, and SpeI restriction enzymes for inverse PCR reaction. After restriction digestion, the DNA was extracted once with Phenol-CHCl$_3$, and once with CHCl$_3$, precipitated with 95% ethanol, and resuspended in TE buffer. Each digested DNA was self-ligated to circularize at a low DNA concentration (2 µg/ml in 500 µl total volume). The ligated DNA was extracted once with Phenol-CHCl$_3$, and once with CHCl$_3$ and precipitated with 95% ethanol. The DNA was used as a template for inverse PCR reaction (95° C. 1 min, 60° C. 1 min, 72° C. 2 min, 30 cycles). One set of primers that annealed to the end of the methylase gene was designed as following: forward primer, 5'CACCGCGATGTCG AGGTAGTCTTC3'(SEQ ID NO:11); reverse primer, 5'GCCTGGAGGCG GAGGCGCAATCCC3'(SEQ ID NO:12). A 1.6 kb inverse PCR product was found in the inverse PCR reaction of the self-ligated PvuI genomic DNA. The inverse PCR product was treated with T4 polynucleotide kinase and T4 DNA polymerase in 50 µl reaction volume (2 µg DNA, 5 µl 10×kinase buffer, 1 µl polynucleotide kinase, 2 µl 0.1 M ATP, 1 µl T4 DNA polymerase, 41 µl TE, 37° C., 1 hour). The DNA was cloned into pUC19. In order to sequence the insert, several deletion clones were constructed (NgoMI & SmaI deletion, BamHI & BstEII deletion, BssHII & BssHII deletion, and AatII & AatII deletion). The DNA sequence was determined using pUC19 forward and reverse primers and customer-made primers. A total of 956 bp sequenced was determined and was translated in all six reading frames. One open reading frame of 684 bp was found with the predicted amino acid sequences MINDQLPRWVR EARVGTRTG . . . (SEQ ID NO:13). 684 bp of DNA has coding capacity of coding for a protein with molecular weight of 26 kD. The N-terminal protein sequence of the partially purified SCaI restriction endonuclease is QLPXXV XXXXXGXXXG (SEQ ID NO:14) (X=non identified residues) . . . . Six residues (shown in bold) are identical between the actual protein sequence and the predicted protein sequence although the actual protein sequence is missing the beginning four residues. The first four residues of the partially purified SCaI protein could be degraded by protease during protein purification. The molecular weight of the partially purified SCaI protein is between 25–26 kD. It was concluded that this 684 bp open reading frame is the SCaI endonuclease gene.

5. Expression of SCaI endonuclease in *E. coli*.

The SCaI methylase gene was amplified by PCR using forward prime 5'CTCGGATCCGGAGGTAAATAAAT-GTCCGGGCGGGACTTT GGATAT3'(SEQ ID NO:15) and reverse primer 5'CGCGGATCCTTAAC ACTCAACTCCTCGCCATCCATA3'(SEQ ID NO:16) (the reverse primer is 85 bp down stream of the methylase stop codon). The PCR DNA was cleaved with BamHI and cloned into the BamHI site of pACYC184 to premodify *E. coli* host. The entire SCaI endonuclease gene was amplified by PCR with two primers. The forward primer contains the ribosome binding site and 6 bp spacing before the ATG start codon (forward primer, 5'TTAGCATGCGGAGGTTTAAAAAT-GATCAACGATCAGCT TCCCCGGTGG3'(SEQ ID NO:17); reverse primer, 5'GGCGCATGCGTT CAGCAC-CGGGGTTT GCGCTTACCT3'(SEQ ID NO:18)). The SCaI endonuclease gene flanked by SphI sites was cloned into the SphI site of expression vector pRRS and transformed into SCaI methylase premodified cells. 500 ml of cells carrying pRRS-SCaIR+and pACYC-SCaIM$^+$ was grown overnight at 30° C. in LB plus Ap (100 µg/ml and Cm (30 µg/ml). Cells were harvested and resupended in 30 ml of sonication buffer. Cell lysis was completed by addition of lysozyme to 100 µg/ml and sonication, Cell debris was removed by centrifugation. The cell extract was diluted 10, 100, 1000, and 10000-fold in TE buffer. 5 µl of the diluted extract was used to digest 1 µg µ DNA for 1 hour at 37° C. The digested DNA was resolved in an 0.8% agarose gel. It was found that the *E. coli* strain carrying pRRS-SCaIR$^+$and pACYC-SCaIM$^+$ makes $10^6$ units of SCaI endonuclease/gram of wet *E. coli* cells.

6. Purification Of The Recombinant SacI Restriction Endonuclease

The recombinant SCaI restriction endonuclease was purified to homogeneity by chromatography using Heparin-Sepharose, DEAE cellulose and Q-Sepharose columns.

A sample of the E. coli containing both pRRS-SCaIR$^+$ and pACYC-SCaIM$^+$ (NEB991) has been deposited under the terms and conditions of the Budapest Treaty with the American Type Culture Collection on Dec. 8, 1995 and received ATCC Accession Number 69966.

What is claimed is:

1. Isolated DNA coding for the SCaI restriction endonuclease, wherein the isolated DNA is obtainable from *Streptomyces caespitosus*.

2. A recombinant DNA vector comprising a vector into which a DNA segment coding for the SCaI restriction endonuclease has been inserted.

3. Isolated DNA coding for the SCaI restriction endonuclease and methylase, wherein the isolated DNA is obtainable from ATCC No. 69966.

4. A cloning vector which comprises the isolated DNA of claim 3.

5. The cloning vector of claim 4, wherein the cloning vector comprises pRRS-SCaIR$^{30}$.

6. A host cell transformed by the cloning vector of claim 2, 4, or 5.

7. A method of producing an SCaI restriction endonuclease comprising culturing a host cell transformed with the vector of claim 2, 4, or 5 under conditions suitable for expression of said endonuclease.

* * * * *

UNITED STATES PATENT AND TRADEMARK OFFICE

CERTIFICATE OF CORRECTION

PATENT NO.: 5,721,126

DATED: February 24, 1998

INVENTOR(S): Xu, et al..

It is certified that errors appear in the above-identified patent and that said Letters Patent is hereby corrected as shown below:

Cover Page, Section [57], line 2, replace "SCaI" with
--ScaI--

Cover Page, Section [57], line 6, replace "SCaI" with
--ScaI--

Cover Page, Section [57], line 7, replace "SCaI" with
--ScaI--

Cover Page, Section [57], line 9, replace "SCaI" with
--ScaI--

Cover Page, Section [57], line 10, replace "SCaI" with
--ScaI--

Cover Page, Section [57], line 11, replace "SCaI" with
--ScaI--

Cover Page, Section [57], line 14, replace "SCaI" with
--ScaI--

Cover Page, Section [57], line 16, replace "SCaI" with
--ScaI--

Cover Page, Section [57], line 18, replace "SCaI" with
--ScaI--

UNITED STATES PATENT AND TRADEMARK OFFICE

CERTIFICATE OF CORRECTION

PATENT NO.: 5,721,126

DATED: February 24, 1998

INVENTOR(S): Xu, et al..

It is certified that errors appear in the above-identified patent and that said Letters Patent is hereby corrected as shown below:

Cover Page, Section [57], line 20, replace "SCaI" with
--ScaI--

Cover Page, Section [57], line 21, replace "SCaI" with
--ScaI--

Column 1, line 7, replace "SCaI" with --ScaI--

Column 1, line 8, replace "SCaI" with --ScaI--

Column 3, line 22, replace "SCaI" with --ScaI--

Column 3, line 26, replace "SCaI" with --ScaI--

Column 3, line 27, replace "SCaI" with --ScaI--

Column 3, line 29, replace "SCaI" with --ScaI--

Column 3, line 30, replace "SCaI" with --ScaI--

Column 3, line 31, replace "SCaI" with --ScaI--

Column 3, line 34, replace "SCaI" with --ScaI--

Column 3, line 36, replace "SCaI" with --ScaI--

UNITED STATES PATENT AND TRADEMARK OFFICE

CERTIFICATE OF CORRECTION

PATENT NO.: 5,721,126          Page 3 of 11

DATED: February 24, 1998

INVENTOR(S): Xu, et al..

It is certified that errors appear in the above-identified patent and that said Letters Patent is hereby corrected as shown below:

Column 3, line 38, replace "SCaI" with --ScaI--

Column 3, line 39, replace "SCaI" with --ScaI--

Column 3, line 43, replace "SCaI" with --ScaI--

Column 3, line 45, replace "SCaI" with --ScaI--

Column 3, line 49, replace "SCaI" with --ScaI--

Column 3, line 51, replace "SCaI" with --ScaI--

Column 3, line 52, replace "SCaI" with --ScaI--

Column 3, line 57, replace "SCaI" with --ScaI--

Column 3, line 61, replace "SCaI" with --ScaI--

Column 3, line 63, replace "SCaI" with --ScaI--

Column 3, line 64, replace "SCaI" with --ScaI--

Column 3, last line, replace "SCaI" with --ScaI--

Column 4, line 3, replace "SCaI" with --ScaI--

Column 4, line 9, replace "SCaI" with --ScaI--

UNITED STATES PATENT AND TRADEMARK OFFICE

CERTIFICATE OF CORRECTION

PATENT NO.: 5,721,126

DATED: February 24, 1998

INVENTOR(S): Xu, et al..

It is certified that errors appear in the above-identified patent and that said Letters Patent is hereby corrected as shown below:

Column 4, line 14, replace "SCaI" with --ScaI--

Column 4, line 22, replace "SCaI" with --ScaI--

Column 4, line 29, replace "hsdR$^{31}$" with --hsdR$^-$--

Column 4, line 29, replace "mcrBC$^{31}$" with --mcrBC$^-$--

Column 4, line 37, replace "SCaI endonuclease, or any SCaI" with --ScaI endonuclease, or any ScaI--

Column 4, line 38, replace "SCaI" with --ScaI--

Column 4, line 40, replace "SCaI" with --ScaI--

Column 4, line 42, replace "SCaI" with --ScaI--

Column 4, line 47, replace "SCaI" with --ScaI--

Column 4, line 48, replace "SCaI" with --ScaI--

Column 4, line 49, replace "SCaI" with --ScaI--

Column 4, line 56, replace "SCaI" with --ScaI--

Column 4, line 61, replace "SCaI" with --ScaI--

Column 4, line 62, replace "SCaI" with --ScaI--

UNITED STATES PATENT AND TRADEMARK OFFICE

CERTIFICATE OF CORRECTION

PATENT NO.: 5,721,126

DATED: February 24, 1998

INVENTOR(S): Xu, et al..

It is certified that errors appear in the above-identified patent and that said Letters Patent is hereby corrected as shown below:

Column 5, line 4, replace "SCaI" with --ScaI--

Column 5, line 12, replace "SCaI" with --ScaI--

Column 5, line 14, replace "SCaI" with --ScaI--

Column 5, line 16, replace "SCaI" with --ScaI--

Column 5, line 20, replace "SCaI" with --ScaI--

Column 5, line 23, replace "SCaI" with --ScaI--

Column 5, line 25, replace "SCaI" with --ScaI--

Column 5, line 27, replace "SCaIR[+]" with --ScaIR[+]--

Column 5, line 29, replace "SCaI endonuclease activity. SCaI" with --ScaI endonuclease activity. ScaI--.

Column 5, line 40, replace "SCaI" with --ScaI--

Column 5, line 43, replace "SCaI" with --ScaI--

Column 5, line 45, replace "SCaI" with --ScaI--

Column 5, line 48, replace "S. caepitosusgenomic" with --S. caepitosus genomic--

UNITED STATES PATENT AND TRADEMARK OFFICE

CERTIFICATE OF CORRECTION

PATENT NO.: 5,721,126            Page 6 of 11

DATED:          February 24, 1998

INVENTOR(S):    Xu, et al..

It is certified that errors appear in the above-identified patent and that said Letters Patent is hereby corrected as shown below:

Column 5, line 57, replace "SCaI" with --ScaI--

Column 5, line 58, replace "SCaI" with --ScaI--

Column 5, line 60, replace "SCaI" with --ScaI--

Column 5, line 61, replace "SCaI" with --ScaI--

Column 5, line 63, replace "Smal" with --SmaI--

Column 5, line 64, replace "SCaI" with --ScaI--

Column 5, line 65, replace "SCaI" with --ScaI--

Column 6, line 1, replace "SCaI" with --ScaI--

Column 6, line 3, replace "SCaI" with --ScaI--

Column 6, line 6, replace "SCaI" with --ScaI--

Column 6, line 7, replace "SCaI" with --ScaI--

Column 6, line 9, replace "din 1::lacZ" with --*din1::lacZ*--

Column 6, line 16, replace "SCaI" with --ScaI--

Column 6, line 18, replace "SCaI" with --ScaI--

UNITED STATES PATENT AND TRADEMARK OFFICE

CERTIFICATE OF CORRECTION

PATENT NO.: 5,721,126

DATED: February 24, 1998

INVENTOR(S): Xu, et al..

It is certified that errors appear in the above-identified patent and that said Letters Patent is hereby corrected as shown below:

Column 6, line 21, replace "SCaI" with --ScaI--

Column 6, line 22, replace "SCaI" with --ScaI--

Column 6, line 24, replace "SCaI" with --ScaI--

Column 6, line 25, replace "SCaI" with --ScaI--

Column 6, line 28, replace "SCaI" with --ScaI--

Column 6, line 39, replace "SCaI" with --ScaI--

Column 6, line 43, replace "SCaI" with --ScaI--

Column 6, line 44, replace "SCaI" with --ScaI--

Column 6, line 46, replace "SCaI" with --ScaI--

Column 6, line 48, replace "Sacl" with --SacI--

Column 6, line 50, replace "SCaI" with --ScaI--

Column 6, line 51, replace "SCaI" with --ScaI--

Column 6, line 52, replace "SCaI" with --ScaI--

Column 6, line 54, replace "Sacl" with --SacI--

Column 6, line 63, replace "SCaI" with --ScaI--

UNITED STATES PATENT AND TRADEMARK OFFICE

CERTIFICATE OF CORRECTION

PATENT NO.: 5,721,126

DATED: February 24, 1998

INVENTOR(S): Xu, et al..

It is certified that errors appear in the above-identified patent and that said Letters Patent is hereby corrected as shown below:

Column 7, line 4, replace "SCaI" with --ScaI--

Column 7, line 5, replace "SCaI" with --ScaI--

Column 7, line 11, replace "PhenoI" with --Phenol--

Column 7, line 27, replace "10Xkinase" with --10X kinase--

Column 7, line38, replace "MINDQLPRWVREARVGTRTG" with
    --MINDQLPRWVREARVGTRTG--

Column 7, line 41, replace "SCaI" with --ScaI--

Column 7, line 42, replace "QLPXXV XXXXXFXXXF" with
    --QLPXXV XXXXXGXXXG--

Column 8, line 1, replace "SCaI" with --ScaI--

Column 8, line 3, replace "SCaI" with --ScaI--

Column 8, line 5, replace "SCaI" with --ScaI--

Column 8, line 6, replace "SCaI" with --ScaI--

Column 8, line 7, replace "SCaI" with --ScaI--

UNITED STATES PATENT AND TRADEMARK OFFICE

CERTIFICATE OF CORRECTION

PATENT NO.: 5,721,126

DATED: February 24, 1998

INVENTOR(S): Xu, et al..

It is certified that errors appear in the above-identified patent and that said Letters Patent is hereby corrected as shown below:

Column 8, line 8-9, replace "ATGTCCGGGCGGGACTTT GGATAT3'"
    with --ATGTCCTGGGCGGGACTTT GGATAT3'--

Column 8, line 15, replace "SCaI" with --ScaI--

Column 8, line 22, replace "SCaI" with --ScaI--

Column 8, line 22, replace "Sphl" with --SphI--

Column 8, line 23, replace "Sphl" with --SphI--

Column 8, line 24, replace "SCaI" with --ScaI--

Column 8, line 25, replace "SCaIR+" with --ScaIR$^+$--

Column 8, line 25, replace "SCaIM$^+$" with --ScaIM$^+$--

Column 8, line 32, replace "$\mu$" with --$\lambda$--

Column 8, line 34, relace "SCaIR$^+$" with --ScaIR$^+$--

Column 8, line 35, replace "SCaIM$^+$" with --ScaIM$^-$--

Column 8, line 35, replace "SCaI" with --ScaI--

UNITED STATES PATENT AND TRADEMARK OFFICE

CERTIFICATE OF CORRECTION

PATENT NO.: 5,721,126

DATED: February 24, 1998

INVENTOR(S): Xu, et al..

It is certified that errors appear in the above-identified patent and that said Letters Patent is hereby corrected as shown below:

Column 8, line 39, replace "SCaI" with --ScaI--

Column 8, line 42, replace "SCaIR$^+$" with --ScaIR$^+$--

Column 8, line 43, replace "SCaIM$^+$" with --ScaIM$^+$--

Column 21, line 23, replace "SCaI" with --ScaI--

Column 21, line 27, replace "SCaI" with --ScaI--

Column 21, line 29, replace "SCaI" with --ScaI--

Column 22, line 23, replace "SCaIR$^{30}$" with --ScaIR$^+$--

Column 22, line 26, replace "SCaI" with --ScaI--

UNITED STATES PATENT AND TRADEMARK OFFICE

CERTIFICATE OF CORRECTION

PATENT NO.: 5,721,126

DATED: February 24, 1998

INVENTOR(S): Xu, et al..

It is certified that errors appear in the above-identified patent and that said Letters Patent is hereby corrected as shown below:

Column 6, line 13, replace "C. Cell" with --C. Cells--

Column 8, line 8, replace "prime" with --primer--

Column 8, line 37, replace "SacI" with --*ScaI*--

Signed and Sealed this

Eleventh Day of August 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 6 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:1:

TTTAAA  6

( 2 ) INFORMATION FOR SEQ ID NO:2:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:2:

```
RGGNCC Y                                                          7
```

( 2 ) INFORMATION FOR SEQ ID NO:3:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:3:

```
CACNNNGTG                                                         9
```

( 2 ) INFORMATION FOR SEQ ID NO:4:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:4:

```
GAATTC                                                            6
```

( 2 ) INFORMATION FOR SEQ ID NO:5:

( i ) SEQUENCE CHARACTERISTICS:
        ( A ) LENGTH: 915 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..915

( x i ) SEQUENCE DESCRIPTION: SEQ ID NO:5:

```
ATG  TCC  GGG  CGG  GAC  TTT  GGA  TAT  GTG  ATA  CAG  TCG  TCC  GCT  GCA  CTA      48
Met  Ser  Gly  Arg  Asp  Phe  Gly  Tyr  Val  Ile  Gln  Ser  Ser  Ala  Ala  Leu
 1              5                        10                       15

TGG  AAT  CGA  CTC  TCT  ACA  TTC  TCA  CAG  AGA  GGA  AAA  GCC  TTG  GAC  ACC      96
Trp  Asn  Arg  Leu  Ser  Thr  Phe  Ser  Gln  Arg  Gly  Lys  Ala  Leu  Asp  Thr
               20                       25                       30

AGG  CTT  GCA  GAC  ATC  AAG  AAG  GCC  CTG  GGG  AAG  CCG  TAC  TAC  GAA  ACC     144
Arg  Leu  Ala  Asp  Ile  Lys  Lys  Ala  Leu  Gly  Lys  Pro  Tyr  Tyr  Glu  Thr
          35                       40                       45

TCG  GAT  GTC  CTT  CTT  TAC  CAC  GGC  GAC  AGT  CTT  GAG  CTG  CTC  AAG  TCA     192
Ser  Asp  Val  Leu  Leu  Tyr  His  Gly  Asp  Ser  Leu  Glu  Leu  Leu  Lys  Ser
     50                       55                       60

ATG  CCT  CAG  CAG  ATT  TTC  GAC  CTT  ACC  GTA  ACT  AGT  CCA  CCT  TAC  AAT     240
Met  Pro  Gln  Gln  Ile  Phe  Asp  Leu  Thr  Val  Thr  Ser  Pro  Pro  Tyr  Asn
```

```
                                          65                      70                                  75                              80
                                         ATT  GGC  AAA  GAG  TAC  GAG  GGT  GTA  CTG  TCG  ATC  GAG  GAA  TAC  ATT  TCC        288
                                         Ile  Gly  Lys  Glu  Tyr  Glu  Gly  Val  Leu  Ser  Ile  Glu  Glu  Tyr  Ile  Ser
                                                             85                       90                       95

TGG  TGC  GAG  ACA  TGG  ATG  TCG  CGC  GTT  CAT  AGG  GCG  ACC  AGC  GCA  GGC        336
                                         Trp  Cys  Glu  Thr  Trp  Met  Ser  Arg  Val  His  Arg  Ala  Thr  Ser  Ala  Gly
                                                        100                      105                     110

GGC  GCA  TTT  TGG  CTC  AAT  GTT  GGG  TAC  GTC  CCT  GTC  CCG  AAC  CAA  GGA        384
                                         Gly  Ala  Phe  Trp  Leu  Asn  Val  Gly  Tyr  Val  Pro  Val  Pro  Asn  Gln  Gly
                                                   115                      120                     125

AAA  GCA  GTC  CCG  ATT  CCT  TAC  CTC  TTG  TGG  GAC  AAG  AGT  CCG  TTC  TAC        432
                                         Lys  Ala  Val  Pro  Ile  Pro  Tyr  Leu  Leu  Trp  Asp  Lys  Ser  Pro  Phe  Tyr
                                              130                      135                     140

ATG  ATC  CAG  GAA  GTT  GTC  TGG  AAT  TAC  GGG  GCG  GGA  GTG  GCG  TCT  CGA        480
                                         Met  Ile  Gln  Glu  Val  Val  Trp  Asn  Tyr  Gly  Ala  Gly  Val  Ala  Ser  Arg
                                         145                      150                     155                     160

AAA  TCG  TTT  TCC  CCG  CGC  AAT  GAA  AAG  TTT  CTC  TGG  TAT  GTG  CGC  GAC        528
                                         Lys  Ser  Phe  Ser  Pro  Arg  Asn  Glu  Lys  Phe  Leu  Trp  Tyr  Val  Arg  Asp
                                                             165                      170                     175

CCG  CTG  AAT  TAT  TAC  TTC  GAC  CTC  GAT  TCG  GTG  CGC  GAC  CCA  AAT  GTG        576
                                         Pro  Leu  Asn  Tyr  Tyr  Phe  Asp  Leu  Asp  Ser  Val  Arg  Asp  Pro  Asn  Val
                                                        180                      185                     190

AAA  TAC  CCC  AAC  CAG  AAA  AAG  AAT  GGG  AAG  CTC  AAA  TGC  AAC  CCG  TTG        624
                                         Lys  Tyr  Pro  Asn  Gln  Lys  Lys  Asn  Gly  Lys  Leu  Lys  Cys  Asn  Pro  Leu
                                                   195                      200                     205

GGG  AAA  AAT  CCC  ACT  GAC  GTT  TGG  CAG  TTC  CCC  AAG  GTT  ACG  TCG  GGC        672
                                         Gly  Lys  Asn  Pro  Thr  Asp  Val  Trp  Gln  Phe  Pro  Lys  Val  Thr  Ser  Gly
                                              210                      215                     220

GCG  AAG  AGA  TCA  AGC  GTG  GAG  CGC  ACC  GCC  CAT  CCG  GCA  CAA  TTC  CCG        720
                                         Ala  Lys  Arg  Ser  Ser  Val  Glu  Arg  Thr  Ala  His  Pro  Ala  Gln  Phe  Pro
                                         225                      230                     235                     240

TCT  GCA  GTC  ATT  GAA  CGG  GTC  ATC  AAG  GCG  TGC  AGC  CCT  TCC  GAC  GGC        768
                                         Ser  Ala  Val  Ile  Glu  Arg  Val  Ile  Lys  Ala  Cys  Ser  Pro  Ser  Asp  Gly
                                                             245                      250                     255

GTC  ATC  CTG  GAC  CCA  TTC  CTC  GGT  TCC  GGA  ACG  ACC  TCG  CTG  ACC  GCC        816
                                         Val  Ile  Leu  Asp  Pro  Phe  Leu  Gly  Ser  Gly  Thr  Thr  Ser  Leu  Thr  Ala
                                                        260                      265                     270

AGA  AAG  CAA  GGC  CGG  TGC  AGC  GTC  GGT  ATC  GAA  ATC  CGC  GAA  GAC  TAC        864
                                         Arg  Lys  Gln  Gly  Arg  Cys  Ser  Val  Gly  Ile  Glu  Ile  Arg  Glu  Asp  Tyr
                                                   275                      280                     285

CTC  GAC  ATC  GCG  GTG  GGA  CGC  CTG  GAG  GCG  GAG  GCG  CAA  TCC  CTC  TTC        912
                                         Leu  Asp  Ile  Ala  Val  Gly  Arg  Leu  Glu  Ala  Glu  Ala  Gln  Ser  Leu  Phe
                                              290                      295                     300

TAG                                                                                   915
                                          *
                                         305
```

( 2 ) INFORMATION FOR SEQ ID NO:6:

( i ) SEQUENCE CHARACTERISTICS:
        ( A ) LENGTH: 304 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ser  Gly  Arg  Asp  Phe  Gly  Tyr  Val  Ile  Gln  Ser  Ser  Ala  Ala  Leu
 1                  5                        10                      15

Trp  Asn  Arg  Leu  Ser  Thr  Phe  Ser  Gln  Arg  Gly  Lys  Ala  Leu  Asp  Thr
              20                       25                      30
```

```
Arg  Leu  Ala  Asp  Ile  Lys  Lys  Ala  Leu  Gly  Lys  Pro  Tyr  Tyr  Glu  Thr
          35                      40                      45

Ser  Asp  Val  Leu  Leu  Tyr  His  Gly  Asp  Ser  Leu  Glu  Leu  Leu  Lys  Ser
     50                      55                      60

Met  Pro  Gln  Gln  Ile  Phe  Asp  Leu  Thr  Val  Thr  Ser  Pro  Pro  Tyr  Asn
65                       70                      75                          80

Ile  Gly  Lys  Glu  Tyr  Glu  Gly  Val  Leu  Ser  Ile  Glu  Glu  Tyr  Ile  Ser
               85                      90                           95

Trp  Cys  Glu  Thr  Trp  Met  Ser  Arg  Val  His  Arg  Ala  Thr  Ser  Ala  Gly
               100                      105                      110

Gly  Ala  Phe  Trp  Leu  Asn  Val  Gly  Tyr  Val  Pro  Val  Pro  Asn  Gln  Gly
          115                      120                      125

Lys  Ala  Val  Pro  Ile  Pro  Tyr  Leu  Leu  Trp  Asp  Lys  Ser  Pro  Phe  Tyr
     130                      135                      140

Met  Ile  Gln  Glu  Val  Val  Trp  Asn  Tyr  Gly  Ala  Gly  Val  Ala  Ser  Arg
145                      150                      155                          160

Lys  Ser  Phe  Ser  Pro  Arg  Asn  Glu  Lys  Phe  Leu  Trp  Tyr  Val  Arg  Asp
                    165                      170                      175

Pro  Leu  Asn  Tyr  Tyr  Phe  Asp  Leu  Asp  Ser  Val  Arg  Asp  Pro  Asn  Val
               180                      185                      190

Lys  Tyr  Pro  Asn  Gln  Lys  Lys  Asn  Gly  Lys  Leu  Lys  Cys  Asn  Pro  Leu
          195                      200                      205

Gly  Lys  Asn  Pro  Thr  Asp  Val  Trp  Gln  Phe  Pro  Lys  Val  Thr  Ser  Gly
     210                      215                      220

Ala  Lys  Arg  Ser  Ser  Val  Glu  Arg  Thr  Ala  His  Pro  Ala  Gln  Phe  Pro
225                      230                      235                          240

Ser  Ala  Val  Ile  Glu  Arg  Val  Ile  Lys  Ala  Cys  Ser  Pro  Ser  Asp  Gly
                    245                      250                      255

Val  Ile  Leu  Asp  Pro  Phe  Leu  Gly  Ser  Gly  Thr  Thr  Ser  Leu  Thr  Ala
               260                      265                      270

Arg  Lys  Gln  Gly  Arg  Cys  Ser  Val  Gly  Ile  Glu  Ile  Arg  Glu  Asp  Tyr
          275                      280                      285

Leu  Asp  Ile  Ala  Val  Gly  Arg  Leu  Glu  Ala  Glu  Ala  Gln  Ser  Leu  Phe
     290                      295                      300
```

( 2 ) INFORMATION FOR SEQ ID NO:7:

( i ) SEQUENCE CHARACTERISTICS:
        ( A ) LENGTH: 684 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..684

( x i ) SEQUENCE DESCRIPTION: SEQ ID NO:7:

```
ATG  ATC  AAC  GAT  CAG  CTT  CCC  CGG  TGG  GTG  CGC  GAG  GCG  CGC  GTG  GGT        48
Met  Ile  Asn  Asp  Gln  Leu  Pro  Arg  Trp  Val  Arg  Glu  Ala  Arg  Val  Gly
1                        5                       10                      15

ACA  AGA  ACA  GGC  GGC  CCT  GCA  ATG  CGC  CCG  AAA  ACT  TCC  GAT  TCG  CCC        96
Thr  Arg  Thr  Gly  Gly  Pro  Ala  Met  Arg  Pro  Lys  Thr  Ser  Asp  Ser  Pro
               20                      25                      30

TAC  TTT  GGA  TGG  GAT  AGC  GAA  GAT  TGG  CCC  GAA  GTG  ACT  CGC  CAG  CTA       144
Tyr  Phe  Gly  Trp  Asp  Ser  Glu  Asp  Trp  Pro  Glu  Val  Thr  Arg  Gln  Leu
          35                      40                      45
```

| | | | | | | | | | | | | | | | | |
|---|---|---|---|---|---|---|---|---|---|---|---|---|---|---|---|---|
| CTG | TCC | GAG | CAA | CCG | CTC | AGC | GGC | GAC | ACG | CTT | GTC | GAT | GCC | GTG | CTC | 192 |
| Leu | Ser | Glu | Gln | Pro | Leu | Ser | Gly | Asp | Thr | Leu | Val | Asp | Ala | Val | Leu | |
| | 50 | | | | | 55 | | | | | 60 | | | | | |
| GCT | TCG | TGG | GAA | TCG | ATC | TTC | GAA | TCC | CGG | CTG | GGG | AGC | GGA | TTT | CAC | 240 |
| Ala | Ser | Trp | Glu | Ser | Ile | Phe | Glu | Ser | Arg | Leu | Gly | Ser | Gly | Phe | His | |
| 65 | | | | | 70 | | | | | 75 | | | | | 80 | |
| ATC | GGC | ACC | CAG | ATC | CGG | CCG | ACT | CCA | CAA | GTA | ATG | GGA | TTC | CTC | CTT | 288 |
| Ile | Gly | Thr | Gln | Ile | Arg | Pro | Thr | Pro | Gln | Val | Met | Gly | Phe | Leu | Leu | |
| | | | | 85 | | | | | 90 | | | | | 95 | | |
| CAT | GCA | CTC | ATC | CCT | CTT | GAG | CTC | GCC | AAC | GGC | GAC | CCG | AGC | TGG | CGC | 336 |
| His | Ala | Leu | Ile | Pro | Leu | Glu | Leu | Ala | Asn | Gly | Asp | Pro | Ser | Trp | Arg | |
| | | | 100 | | | | | 105 | | | | | 110 | | | |
| GCG | GAC | CTG | AAT | TCC | TCC | GAA | AAG | GAT | CTC | GTG | TAT | CAG | CCG | GAT | CAT | 384 |
| Ala | Asp | Leu | Asn | Ser | Ser | Glu | Lys | Asp | Leu | Val | Tyr | Gln | Pro | Asp | His | |
| | | | 115 | | | | | 120 | | | | | 125 | | | |
| AAA | TAT | TCA | ATC | GAG | ATG | AAA | ACC | TCG | TCA | CAC | AAG | GAT | CAA | ATT | TTC | 432 |
| Lys | Tyr | Ser | Ile | Glu | Met | Lys | Thr | Ser | Ser | His | Lys | Asp | Gln | Ile | Phe | |
| | | 130 | | | | | 135 | | | | | 140 | | | | |
| GGC | AAC | CGA | AGC | TTC | GGA | GTC | GAG | AAT | CCC | GGC | AAG | GGA | AAG | AAG | GCA | 480 |
| Gly | Asn | Arg | Ser | Phe | Gly | Val | Glu | Asn | Pro | Gly | Lys | Gly | Lys | Lys | Ala | |
| 145 | | | | | 150 | | | | | 155 | | | | | 160 | |
| AAG | GAC | GGC | TAT | TAT | GTG | GCG | GTA | AAC | TTC | GAA | AAA | TGG | AGT | GAC | GCT | 528 |
| Lys | Asp | Gly | Tyr | Tyr | Val | Ala | Val | Asn | Phe | Glu | Lys | Trp | Ser | Asp | Ala | |
| | | | | 165 | | | | | 170 | | | | | 175 | | |
| CCG | GGC | AGA | CTT | CCA | CGC | ATC | CGG | ACG | ATC | CGC | TAT | GGG | TGG | CTT | GAC | 576 |
| Pro | Gly | Arg | Leu | Pro | Arg | Ile | Arg | Thr | Ile | Arg | Tyr | Gly | Trp | Leu | Asp | |
| | | | 180 | | | | | 185 | | | | | 190 | | | |
| CAT | ACA | GAT | TGG | GTG | GCG | CAG | AAA | TCT | CAA | ACG | GGC | CAG | CAG | TCG | TCA | 624 |
| His | Thr | Asp | Trp | Val | Ala | Gln | Lys | Ser | Gln | Thr | Gly | Gln | Gln | Ser | Ser | |
| | | 195 | | | | | 200 | | | | | 205 | | | | |
| CTA | CCG | GCC | GTC | GTA | TCC | AAC | ACT | CAA | CTC | CTC | GCC | ATC | CAT | ACG | GGT | 672 |
| Leu | Pro | Ala | Val | Val | Ser | Asn | Thr | Gln | Leu | Leu | Ala | Ile | His | Thr | Gly | |
| | 210 | | | | | 215 | | | | | 220 | | | | | |
| GGC | CAG | AGG | TAA | | | | | | | | | | | | | 684 |
| Gly | Gln | Arg | * | | | | | | | | | | | | | |
| 225 | | | | | | | | | | | | | | | | |

( 2 ) INFORMATION FOR SEQ ID NO:8:

( i ) SEQUENCE CHARACTERISTICS:
        ( A ) LENGTH: 227 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Ile | Asn | Asp | Gln | Leu | Pro | Arg | Trp | Val | Arg | Glu | Ala | Arg | Val | Gly |
| 1 | | | | 5 | | | | | 10 | | | | | 15 | |
| Thr | Arg | Thr | Gly | Gly | Pro | Ala | Met | Arg | Pro | Lys | Thr | Ser | Asp | Ser | Pro |
| | | | 20 | | | | | 25 | | | | | 30 | | |
| Tyr | Phe | Gly | Trp | Asp | Ser | Glu | Asp | Trp | Pro | Glu | Val | Thr | Arg | Gln | Leu |
| | | 35 | | | | | 40 | | | | | 45 | | | |
| Leu | Ser | Glu | Gln | Pro | Leu | Ser | Gly | Asp | Thr | Leu | Val | Asp | Ala | Val | Leu |
| | 50 | | | | | 55 | | | | | 60 | | | | |
| Ala | Ser | Trp | Glu | Ser | Ile | Phe | Glu | Ser | Arg | Leu | Gly | Ser | Gly | Phe | His |
| 65 | | | | | 70 | | | | | 75 | | | | | 80 |
| Ile | Gly | Thr | Gln | Ile | Arg | Pro | Thr | Pro | Gln | Val | Met | Gly | Phe | Leu | Leu |
| | | | | 85 | | | | | 90 | | | | | 95 | |
| His | Ala | Leu | Ile | Pro | Leu | Glu | Leu | Ala | Asn | Gly | Asp | Pro | Ser | Trp | Arg |
| | | | 100 | | | | | 105 | | | | | 110 | | |

```
Ala Asp Leu Asn Ser Ser Glu Lys Asp Leu Val Tyr Gln Pro Asp His
        115                 120                 125

Lys Tyr Ser Ile Glu Met Lys Thr Ser Ser His Lys Asp Gln Ile Phe
    130             135                 140

Gly Asn Arg Ser Phe Gly Val Glu Asn Pro Gly Lys Gly Lys Lys Ala
145             150                 155                     160

Lys Asp Gly Tyr Tyr Val Ala Val Asn Phe Glu Lys Trp Ser Asp Ala
                165             170                     175

Pro Gly Arg Leu Pro Arg Ile Arg Thr Ile Arg Tyr Gly Trp Leu Asp
            180                 185                 190

His Thr Asp Trp Val Ala Gln Lys Ser Gln Thr Gly Gln Gln Ser Ser
        195             200                 205

Leu Pro Ala Val Val Ser Asn Thr Gln Leu Leu Ala Ile His Thr Gly
    210                 215                 220

Gly Gln Arg
225
```

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:9:

```
Ser Pro Pro Tyr
1
```

( 2 ) INFORMATION FOR SEQ ID NO:10:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:10:

```
Asp Pro Phe Leu Gly Ser Gly Thr Thr
1               5
```

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:11:

CACCGCGATG TCGAGGTAGT CTTC                         24

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:12:

GCCTGGAGGC GGAGGCGCAA TCCC  24

( 2 ) INFORMATION FOR SEQ ID NO:13:

( i ) SEQUENCE CHARACTERISTICS:
( A ) LENGTH: 20 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:13:

```
Met Ile Asn Asp Gln Leu Pro Arg Trp Val Arg Glu Ala Arg Val Gly
1               5                   10                  15
Thr Arg Thr Gly
            20
```

( 2 ) INFORMATION FOR SEQ ID NO:14:

( i ) SEQUENCE CHARACTERISTICS:
( A ) LENGTH: 16 amino acids
( B ) TYPE: amino acid
( C ) STRANDEDNESS: single
( D ) TOPOLOGY: unknown ( i i ) MOLECULE TYPE: protein ( x i ) SEQUENCE DESCRIPTION: SEQ ID NO:14:

```
Gln Leu Pro Xaa Xaa Val Xaa Xaa Xaa Xaa Xaa Gly Xaa Xaa Xaa Gly
1               5                   10                  15
```

( 2 ) INFORMATION FOR SEQ ID NO:15:

( i ) SEQUENCE CHARACTERISTICS:
( A ) LENGTH: 45 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:15:

CTCGGATCCG GAGGTAAATA AATGTCCGGG CGGGACTTTG GATAT  45

( 2 ) INFORMATION FOR SEQ ID NO:16:

( i ) SEQUENCE CHARACTERISTICS:
( A ) LENGTH: 36 base pairs
( B ) TYPE: nucleic acid
( C ) STRANDEDNESS: single
( D ) TOPOLOGY: unknown ( i i ) MOLECULE TYPE: DNA (genomic)

( x i ) SEQUENCE DESCRIPTION: SEQ ID NO:16:

CGCGGATCCT TAACACTCAA CTCCTCGCCA TCCATA  36

( 2 ) INFORMATION FOR SEQ ID NO:17:

( i ) SEQUENCE CHARACTERISTICS:
( A ) LENGTH: 48 base pairs
( B ) TYPE: nucleic acid
( C ) STRANDEDNESS: single
( D ) TOPOLOGY: unknown (i i) MOLECULE TYPE: DNA (genomic)

(x i) SEQUENCE DESCRIPTION: SEQ ID NO:17:

TTAGCATGCG GAGGTTTAAA AATGATCAAC GATCAGCTTC CCCGGTGG    48

(2) INFORMATION FOR SEQ ID NO:18:

(i) SEQUENCE CHARACTERISTICS:
    (A) LENGTH: 36 base pairs
    (B) TYPE: nucleic acid
    (C) STRANDEDNESS: single
    (D) TOPOLOGY: unknown (i i) MOLECULE TYPE: DNA (genomic)

(x i) SEQUENCE DESCRIPTION: SEQ ID NO:18:

GGCGGATCCG TTCAGCACCG GGGTTTGCGC TTACCT    36